US005455178A

United States Patent [19]
Fattinger

[11] Patent Number: 5,455,178
[45] Date of Patent: Oct. 3, 1995

[54] MICROOPTICAL SENSOR AND METHOD

[75] Inventor: Christof Fattinger, Blauen, Switzerland

[73] Assignee: Hoffmann-La Roche Inc., Nutley, N.J.

[21] Appl. No.: 69,687

[22] Filed: May 28, 1993

Related U.S. Application Data

[63] Continuation of Ser. No. 902,774, Jun. 23, 1992, abandoned, which is a continuation of Ser. No. 692,760, Apr. 29, 1991, abandoned.

[30] Foreign Application Priority Data

May 3, 1990 [CH] Switzerland ............................ 1501/90

[51] Int. Cl.⁶ ...................................................... G01N 21/01
[52] U.S. Cl. ............................ 436/164; 385/12; 385/30; 385/37; 422/82.08; 422/82.09; 422/82.11; 436/518; 436/527; 436/805
[58] Field of Search ...................................... 356/128, 136, 356/328; 359/566, 569, 573, 574, 885, 888, 637, 640, 890, 896, 572; 385/10, 12, 30, 36, 37, 129; 422/82.05, 82.09, 82.11; 436/164, 805, 518, 527

[56] References Cited

U.S. PATENT DOCUMENTS

| 3,791,737 | 2/1974 | Johansson | 356/328 X |
|---|---|---|---|
| 3,982,810 | 9/1976 | Tamir et al. | 385/37 |
| 4,047,795 | 9/1977 | Hughes et al. | 385/37 |
| 4,082,425 | 4/1978 | Miller | 385/37 |
| 4,102,560 | 7/1978 | Miller | 385/30 X |

(List continued on next page.)

FOREIGN PATENT DOCUMENTS

| 112721 | 12/1983 | European Pat. Off. . | |
|---|---|---|---|
| 63-276004 | 11/1988 | Japan . | |
| 1-252902 | 10/1989 | Japan | 359/569 |
| 2209408 | 5/1989 | United Kingdom . | |
| 89/07756 | 8/1989 | WIPO . | |
| 89/09394 | 10/1989 | WIPO . | |

OTHER PUBLICATIONS

M. L. Dakss et al. *Appl. Phys. Lett.* 1970, 16, 523–525.
L. F. Johnson et al. *Appl. Phys. Lett.* 1981, 38, 532–534.
R. C. McPhedran et al. *J. Opt.* 1982, 13, 209–218.
W. Lukosz et al. *Opt. Lett.* 1983, 8, 537–539.
K. Tiefenthaler et al. *J. Opt. Soc. Am. B* 1989, 6, 209–220.
S. T. Peng *J. Opt. Soc. Am. A.* 1990, 7, 1448–1456.
Tiefenthaler et al. "Integrated Optical Switches and Gas Sensors", *Optics Letters*, 1984, 9, 137–139.
Derwent Abstract No. 84–166401 of EP 112 721.
Tamir et al., Journal of the Optical Society of America, 61(10), 1397–1413, (1971).
Sensors and Activators, 4, pp. 299–304 (1983).
Phys. Med. Biol., 22(3), 442–430 (1977).
Analytical Biochemistry, 84, 56–67 (1978).
Patent Abstracts of Japan, 13(93) 838, (3441), 1989.
Soviet Physics Technical Physics; 34(7), 749–752, (1989).
Tamir, T. et al., Appl. Phys. 14: 235–254, (1977).

*Primary Examiner*—James C. Housel
*Assistant Examiner*—Arlen Soderquist
*Attorney, Agent, or Firm*—George M. Gould; George W. Johnston

[57] ABSTRACT

A microoptical sensor and a corresponding method for detecting chemical substances in a sample. The sample is brought into contact with the waveguiding layer of a planar optical waveguide. Coherent light is coupled into the waveguiding layer, propagates therein as a guided wave, and the latter is decoupled from the waveguiding layer. Both, coupling and decoupling of the light wave guided in the planar waveguide is effected by means of a multi-diffractive grating situated in the plane of the layer, i.e. a grating structure comprising two or more fundamental frequency components for in-coupling and out-coupling, respectively. The multi-diffractive grating coupler results in a directional separation of decoupled light from reflected, transmitted and directly diffracted sub-beams, respectively. This makes possible a background-free detection of guided light decoupled from the waveguiding layer, although the regions on the waveguiding layer in which coupling and decoupling of the guided light wave take place overlap in part.

21 Claims, 5 Drawing Sheets

U.S. PATENT DOCUMENTS

| | | | |
|---|---|---|---|
| 4,262,996 | 4/1981 | Yao | 385/37 |
| 4,426,130 | 1/1984 | Knop | 359/569 X |
| 4,528,448 | 7/1985 | Doggett | 359/572 X |
| 4,647,544 | 3/1987 | Nicoli et al. | 436/805 X |
| 4,697,878 | 10/1987 | Kimura et al. | 359/574 |
| 4,815,843 | 3/1989 | Tiefenthaler et al. | 356/128 |
| 4,876,208 | 10/1989 | Gustafson et al. | 436/164 X |
| 4,877,747 | 10/1989 | Stewart | 422/82.11 X |
| 4,882,288 | 11/1989 | North et al. | 436/525 |
| 4,886,341 | 12/1989 | Oishi et al. | 359/572 X |
| 4,931,384 | 6/1990 | Layton et al. | 436/164 X |
| 5,006,716 | 4/1991 | Hall | 436/171 X |
| 5,082,629 | 1/1992 | Burgess, Jr. et al. | 422/82.11 |
| 5,132,097 | 7/1992 | Van Deusen et al. | 422/82.09 |

MICROOPTICAL SENSOR AND METHOD

This application is a continuation of U.S. application Ser. No. 07/902,774, filed Jun. 23, 1992, which is a continuation of U.S. application Ser. No. 07/692,760, filed Apr. 29, 1991, both now abandoned.

BACKGROUND OF THE INVENTION

The invention relates to a microoptical sensor for detecting chemical substances, this sensor having a planar optical waveguide which comprises a solid substrate having layered on its top surface a waveguiding layer and a diffraction grating, situated on or in the immediate vicinity of the waveguiding layer, for coupling and decoupling coherent light applied thereto.

The invention further relates to a microoptical method for detecting chemical substances with a microoptical sensor of the kind indicated above, which method comprises contacting the surface of the planar optical waveguide with a sample containing the substance to be detected, coupling coherent light into said waveguiding layer, which light propagates therein as a guided light wave, then decoupling said light wave out of the waveguiding layer.

Chemical changes, e.g. molecular additions, at or in the immediate vicinity of the waveguiding layer are detected, for example, by measuring the relative intensity of the decoupled beams of light. An alternative detection method comprises simultaneously coupling into the waveguide two coherent (e.g. orthogonally polarized) beams of light and measuring the relative phase (phase difference) of two decoupled beams by interference of said sub-beams, which are generated by the two jointly excited (orthogonally polarized) modes in the waveguide.

Many of the conventional test methods used in biomedical diagnosis are based on the use of solid carrier substrates, e.g. balls or pellets, coated with a chemo-sensitive molecular coating. For analysis, the patient's sample, e.g. serum or plasma, is brought into contact with the carrier substrate. Molecules, e.g. biomolecules, dissolved in the sample, and required to be detected, enter into a specific bond with the chemo-sensitive coating. Typically, the chemo-sensitive coating consists of biomolecular recognition elements, such as antibodies, receptors, enzymes or DNA-strands.

In conventional tests, detection of the molecules bound to the chemosensitive coating is usually effected indirectly by means of a second dissolved reaction partner labelled with a radio isotope, a fluorophore or an enzyme. The labelled molecules have the specific property of coupling to those binding sites which have been left unoccupied on the chemo-sensitive coating, or of coupling to the free end of the molecules to be detected, which in turn bind to the chemo-sensitive coating, the latter is called "sandwich" technique. The resulting concentration of the labelled molecules on the carrier substrate is determined by a suitable measurement technique. The concentration of the substance to be detected in the sample is concluded therefrom.

Planar optical waveguides consist of a thin dielectric layer or coating on a transparent carrier substrate. (For a tutorial introduction see, for example T. Tamir, Integrated Optics, Springer, Berlin 1985). The medium covering the waveguiding layer is known as the superstrate and may, for example, be gaseous or liquid. Light, e.g. a laser beam, coupled into the waveguide is guided by total internal reflection in the waveguiding layer, provided the substrate and the superstrate have a lower refractive index than the dielectric layer therebetween. The propagation of the optical wave in the waveguide is restricted to a number of discrete modes. The phase velocity of the guided light wave is $c/N$, where c is the velocity of light in vacuum and N is the effective refractive index of the excited waveguide mode. The effective refractive index N depends on the optical parameters of the waveguiding structure, i.e. on the thickness and refractive index of the thin waveguiding layer and on the refractive indices of the substrate and superstrate material. The transverse field distribution of the modes rapidly falls off outside the waveguiding layer. The effective thickness $d_{eff}$ of the waveguide is defined as the sum of the geometric thickness d of the waveguiding layer and the penetration depths of the evanescent fields into the substrate and the superstrate. By the use of suitable high-refractive materials for the waveguiding layer, waveguides with a $d_{eff}$ of less than one wavelength of the guided light can be realized. Under these conditions the penetration depth of the evanescent fields into the substrate and superstrate is only a fraction of the wavelength.

The field of the guided mode, which is highly spatially confined at the substrate surface, is ideally suited for sensing chemical changes taking place at or in the immediate vicinity of the waveguiding layer. Optical measurement techniques based on a waveguiding structure, also known as "integrated-optical" techniques, are increasingly gaining significance for surface analysis and optical sensor systems. Sensing schemes are known in which changes of the propagation constant (effective refractive index) of the guided modes, and/or changes in light intensity caused by absorption of the guided modes are utilized to detect (chemical) changes at the interface between the waveguiding layer and the superstrate and/or in the volume of the waveguiding layer.

Selective detection of specific substances in the sample covering the waveguide is achieved by an additional chemosensitive layer on the wave-guiding layer. Such additional layer is capable of binding selectively the molecules to be detected. This results for example, in a change of the effective refractive index of the guided mode. The interaction of the guided mode with the sample takes place via the evanescent field, whose penetration depth into the superstrate is typically greater than the thickness of the additional chemo-sensitive layer.

According to the known prior art, the light is coupled into the waveguide by focusing a laser beam on its end face (butt-face coupling), or by means of a diffraction grating (grating coupling), in the latter case the beam to be coupled is incident on the waveguiding layer from the side of the substrate or superstrate. Butt-face coupling makes great demands upon the mechanical positioning of the coupling lens, particularly for extremely thin surface-sensitive waveguides with a $d_{eff}$ of less than 1 micrometer. With grating couplers it is possible easily to couple a laser beam into and decouple it from a waveguide without the use of focusing optics.

Arrangements are known in which laterally bounded grating structures on the waveguiding layer are used for coupling an incident beam into the waveguides or decoupling an excited waveguide mode. A laser beam is coupled in if it meets the region of the waveguide provided with the grating structure at a specific angle of incidence dependent upon the grating period and the effective refractive index. The excited mode passes, for example, through a portion of the waveguide situated between two spatially separated grating regions and is decoupled on meeting the second grating region.

By measuring the intensity of the decoupled guided mode, the absorption by molecules situated at the surface of the waveguide can be detected with high sensitivity. Coupling of the incident wave to the guided wave comes into effect only within the area of the grating region. Coupling and decoupling via the grating has the character of a resonance. The resonance angle for optimal coupling is dependent upon the grating period and on the effective refractive index of the guided mode. A change of the effective refractive index, due e.g. to addition of molecules at the surface of the waveguide, results in a shift of the angle of resonance at which the laser beam is coupled in or decoupled. By measuring the angle of incidence at which the guided wave can be excited, a molecular surface coverage in the grating region of the waveguiding layer can be detected with submonomolecular sensitivity (cf. K. Tiefenthaler and W. Lukosz, "Integrated optical switches and gas sensors", Optics Letters vol. 9, No. 4, 1984, pp. 137–139, and K. Tiefenthaler and W. Lukosz, U.S. Pat. No. 4,815,843, 1989).

Another well-known technique for detecting adsorbate layers is based on the optical excitation of surface plasmons at the surface of a thin metal layer with or without the use of a diffraction grating. The coherent excitation of the free electrons of a metal in the form of a surface wave propagating along the surface of the metal is known as surface plasmon. The electromagnetic field of the surface plasmon is spatially confined at the metal surface. The transverse field distribution has a maximum at the surface and falls off exponentially in the metal and in the superstrate. The plasmon wave is damped by ohmic losses in the metal. The propagation distance of the surface plasmon is, for example, 22 micrometers for pure silver at a wavelength of 514 nm. If molecules adsorb at the metal surface, the propagation constant (phase velocity) of the surface plasmon propagating along the interface changes.

The sensitivity with which this change of the propagation constant can be measured is limited by the relatively short propagation distance of the surface plasmon. Various optical configurations are known which utilize the resonant excitation of surface plasmons in order to detect molecular adsorbate layers on metal surfaces (cf. see B. Liedberg, C. Nylander, and I. Luridstrom, "Surface plasmon resonance for gas detection and biosensing", Sensors and Actuators 4, 1983, pp. 299–304 and EP 0 112 721).

A universal method of characterising thin layers on planar surfaces is ellipsometry, which is based on the measurement of the state of polarization of light reflected at the surface. A light beam impinging on the surface at a certain angle of incidence experiences on reflection a change in the relative amplitude and phase of the electromagnetic field components polarized parallel and perpendicular to the plane of incidence. The incident beam of light is preferably circularly or linearly polarized. The state of polarization of the generally elliptically polarized reflected beam is analysed. This information is used to determine the thickness and the refractive index of the thin layer (cf. R. Azzam et al., Physics in Medicine and Biology 22, 1977, 422–430, P. A. Cuypers et al., Analytical Biochemistry 84, 1978, 56–57).

Upon a single reflection of the beam at the surface for analysis, the changes in the state of polarization due to a molecular adsorbate layer is very small. This can be explained by the fact that the interaction of the incident beam with the adsorbate layer is restricted to a distance of the order of the layer thickness. Minor changes in the state of polarization after the passage of the incident and reflected beam through the substrate carrying the adsorbate layer to be detected, or after the passage of a cell attached to the substrate and containing the sample fluid, restrict the accuracy of an ellipsometric measurement.

SUMMARY OF THE INVENTION

The object of this invention is to provide a high-sensitivity optical measuring technique with which molecular changes at surfaces and interfaces can be easily detected.

According to the invention, this problem is solved by a microoptical sensor of the kind referred to in the preamble, wherein said diffraction grating comprises a multi-diffractive grating structure.

A microoptical method according to the invention, i.e. a method for detecting chemical substances with a microoptical sensor according to the invention comprises contacting the surface of the planar optical waveguide with a sample containing the substance to be detected, coupling coherent light into said waveguiding layer, which light propagates therein as a guided light wave, then decoupling said light wave out of the waveguiding layer, and analyzing the decoupled light.

A grating structure is multi-diffractive if its frequency spectrum comprises a plurality of fundamental components. By suitable choice of the geometry of the multi-diffractive grating structure it is possible to vary the diffraction angles and the intensities of the discrete diffraction orders independently of one another.

Of particular interest here is the bidiffractive grating coupler which has two independent diffraction orders. The two fundamental frequency components of the bidiffractive grating structure differ from one another preferably by less than a factor of two. Bidiffractive grating structures can be embodied, for example, by superposing two gratings of different periodicity. This can be done, for example, by means of a two-stage lithographic process in which two surface relief gratings of different periodicity are etched in sequence into a substrate surface.

Prior art grating couplers consist of a "classic" diffraction grating, whose diffraction orders are allocated multiples of the fundamental frequency of the grating. The 1st diffraction order is produced by the fundamental frequency of the grating, which is determined by the reciprocal value of the grating constant.

The method according to the invention has the advantage that at least one decoupled sub-beam is generated which does not coincide with a direct diffraction order of the pencil of rays incident on the grating structure.

The use of a multidiffractive grating structure in a microoptical sensor according to the invention enables a separation of the sub-beam decoupled from the waveguide from reflected, transmitted or directly diffracted subbeams, although the regions on the waveguide layer in which the coupling and decoupling of the beams of light take place partially overlap.

DETAILED DESCRIPTION OF THE INVENTION

The invention can be better understood with reference to the accompanying drawings.

Figure 1A:
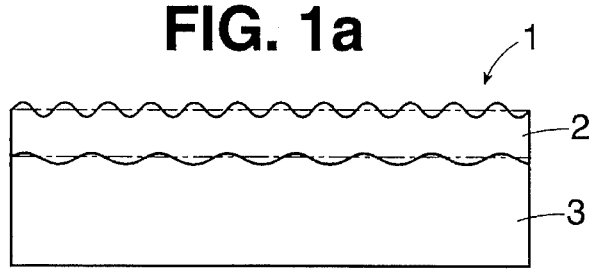
FIGS. 1a–1e are diagrammatic sections of different forms of planar waveguides with multi-diffractive grating couplers.

The planar waveguide 1 illustrated diagrammatically in section in FIG. 1a consists of a waveguiding layer 2 on a planar substrate 3. The surface of the waveguiding layer 2 and the interface between the waveguiding layer 2 and the substrate 3 are each modulated with a surface relief grating. The two optical diffraction gratings may also be present inside the waveguiding layer, e.g. beneath the surface thereof.

Figure 1B:
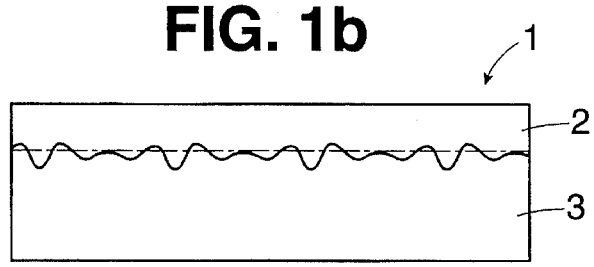

The planar waveguide 1 illustrated in section in FIG. 1b also consists of a waveguiding layer 2 on a substrate 3. In this alternative form, however, only the interface between the waveguiding layer 2 and the substrate 3 is modulated with a biperiodic grating structure. The biperiodic grating structure consists, for example, of a superposition (or mixture) of two sinusoidal gratings having different periodicity.

Figure 1C:
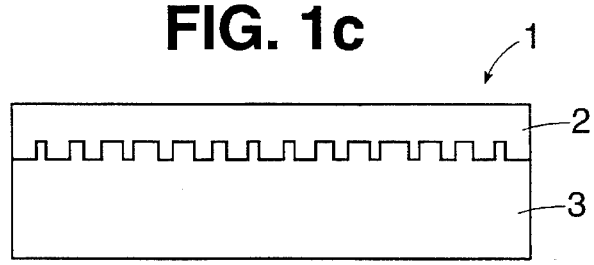

Similarly, the planar waveguide shown in FIG. 1c consists of the wave-guiding layer 2 and the substrate 3 and an optical diffraction grating. The bidiffractive property of the grating is obtained by suitable choice of the grating structure. In this case, the profile of consecutive grating grooves may be periodically varied in width (pulse width modulation) and/or in depth (pulse amplitude modulation). The grating grooves are hereinafter also subsumed under the term grating elements.

Figure 1D:
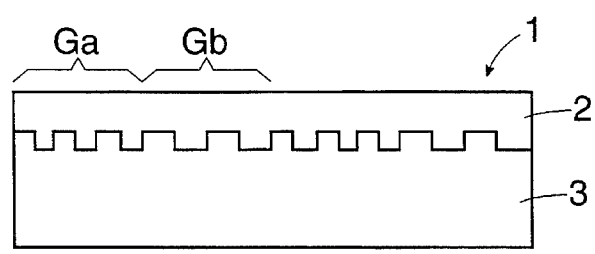

The planar waveguide shown in FIG. 1d consists of a waveguiding layer 2 on a substrate 3, the interface again being modulated with a grating structure. The grating structure is composed of alternate sections Ga and Gb of two gratings of different periodicity.

Figure 1E:
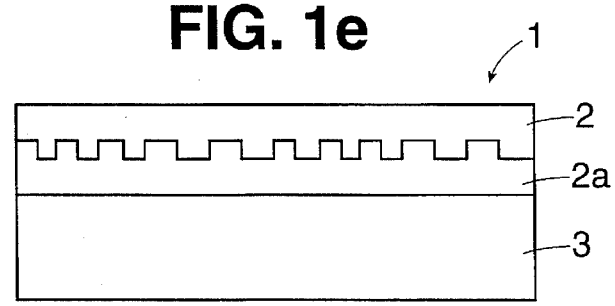

Similarly, the planar waveguide 1 shown in FIG. 1e comprises a waveguiding layer 2 and a substrate 3, and a bidiffractive grating structure. In this embodiment, however, there is an intermediate layer 2a between the waveguiding layer and the substrate. The interface between the waveguiding layer 2 and the intermediate layer 2a is modulated with the grating. To produce the grating structure, the layer 2a is first applied to the planar o substrate 3. In a second step a surface relief grating is formed in the layer 2a by an embossing process. Alternatively to embossing, the surface relief grating can also be prepared by microlithography. In a third step the waveguiding layer 2 of high refractive index is deposited on top of layer 2a which carries the surface relief.

The materials from which the waveguiding layers are made are known in the art, e.g., an oxide layer such as $SiO_2$, $TiO_2$, $ZrO_2$, $SnO_2$, $Nb_2O_5$, $Ta_2O_5$, $Si_3N_4$, $FePO_4$ and mixtures hereof or polymeric layers such as polystyrole, polycarbonate, polyimide, PMMA, polyurethane, etc..

A master grating for the embossing process as well as the multi diffractive grating structure can also be produced holographically.

Figure 2A:
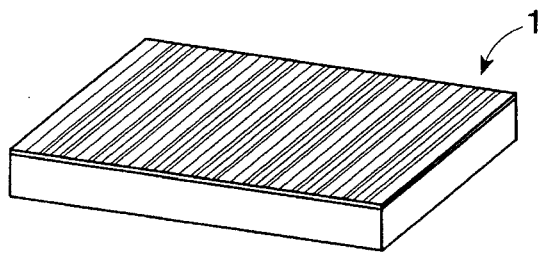
FIGS. 2a and 2b are perspective views of embodiments of planar waveguides with multi-diffractive grating couplers.
Figure 2B:
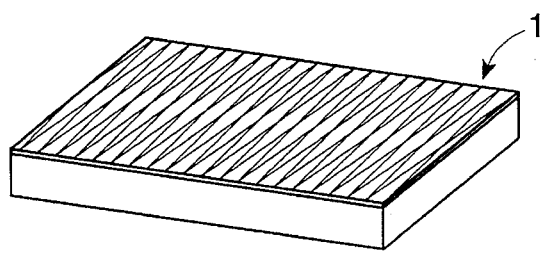

The waveguide I shown diagrammatically in perspective in FIG. 2a is modulated with two gratings. The two superposed gratings are arranged parallel to one another and have different periodicity The planar waveguide 1 shown in FIG. 2b is also modulated with two superposed gratings. Unlike the embodiment shown in FIG. 2a, however, the superposed gratings have different orientations. Grating structures of this kind are known as crossed gratings.

A beam of light is coupled into the waveguiding layer 2 by diffraction gratings whose grating constant is smaller than the vacuum wavelength of the light to be coupled. The diffraction orders of such fine gratings are transversely damped (evanescent) waves, which propagate along the grating. Provided that the angle of incidence is correctly chosen, the beam of light impinging on the grating is coupled into the waveguide via one of these evanescent diffraction orders. If, as shown in FIGS. 3a and 3b, however, a grating of this kind is immersed in a immersion liquid 1 of high refractive index (e.g. diidomethane with refractive index n=1.73), then instead of the evanescent waves freely propagating beams of light occur, the diffraction angles of which are observable.

The mode of operation of a bidiffractive diffraction grating is explained by reference to an example in FIG. 3a. The incident beam of light is split up into a number of sub-beams as a result of diffraction at the grating structure. The sub-beams diffracted at the angles $\theta_a$ and $\theta_b$ are generated by the grating $G_a$ and $G_b$ respectively. The non-diffracted transmitted beam corresponds to the zero diffraction order in transmission. By suitable choice of the geometry of the grating structure it is possible to define the diffraction angle $\theta_a$ and $\theta_b$ of the diffracted sub-beams independently of one another.

Figure 3A:
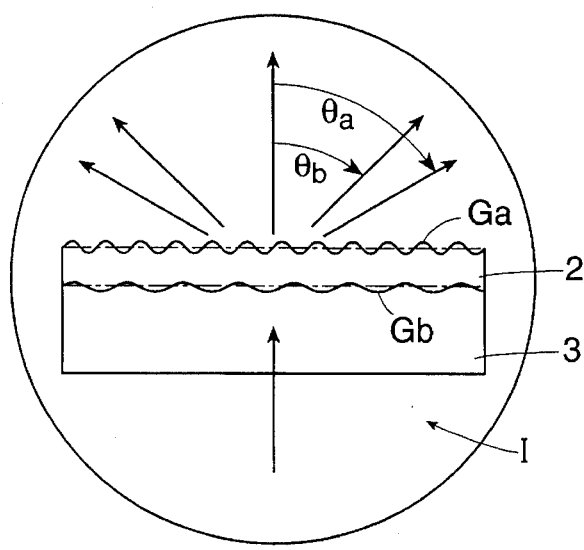
FIGS. 3a and 3b are diagrammatic illustrations of the optical properties of a bidiffractive diffraction grating and an ordinary grating having two diffraction orders.
Figure 3B:
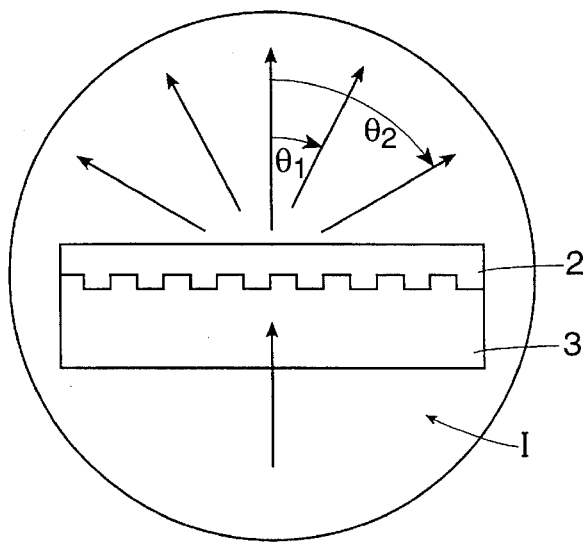

FIG. 3b shows the optical properties of a grating coupler with a diffraction grating according to the prior art. A beam of light impinging on the grating is split up by diffraction into a number of sub-beams. In addition to the first diffraction order other discrete orders may occur, which are generated by the higher Fourier components (harmonics) of the grating profile, which can be rectangular for example. The diffraction angles $\theta_j$ of the discrete diffraction orders satisfy the grating diffraction equation $\sin(\theta_j) = j(\lambda/nl)$, which includes the diffraction order j, the vacuum wavelength $\lambda$, the refractive index n of the medium I surrounding the grating and the grating constant l (small letter L).

If the high-refractive immersion liquid I shown in FIGS. 3a and 3b is replaced by a medium I having a lower refractive index n (e.g. water with n= 1.33 or air with n=1), then instead of the diffracted sub-beams evanescent waves occur, which propagate along the interface between the waveguiding layer 2 and the medium I. The incident beam is coupled into the waveguide 2 if it impinges on the grating coupler at a distinct angle which is dependent upon the grating period and the effective refractive index of the waveguide.

Figure 4:
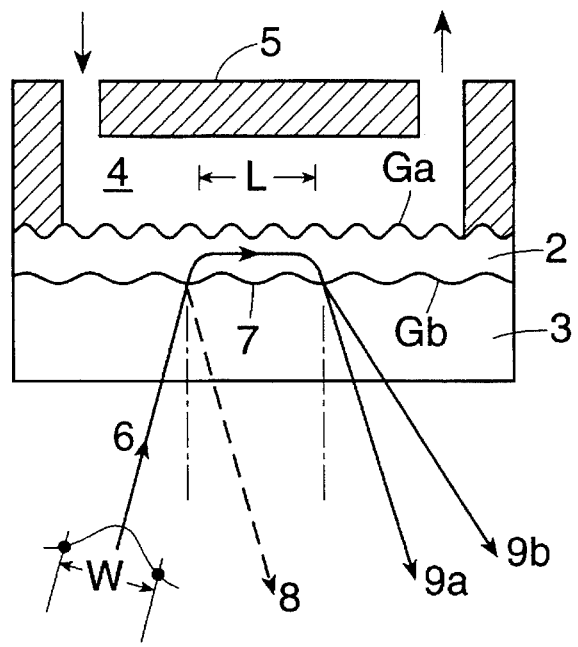
FIG. 4 is a diagrammatic section of a sensor according to the invention.

The sensor shown in section in FIG. 4 consists of the planar waveguide 1 and a sample cell 5 disposed thereon comprising side walls and a cover. The cover has apertures through which the interior of the sample cell 5 and hence the sensitive surface of the waveguide is charged with the substance 4 under examination.

FIG. 4 and the subsequent Figures also show the path of the light during the measurement. As shown in FIG. 4, a beam of light 6 entering from the substrate side is coupled partially into the waveguide 1 by one of the two gratings Ga and Gb. The coupled sub-beam 7 propagates, as a guided mode, through the section L of the waveguiding layer 2 interacting on its path (of length L) with the sample 4. The direction of one of the two decoupled subbeams 9a and 9b differs from the direction of the non-coupled fraction 8 of the incident beam 6, such fraction being reflected at the waveguiding layer 2. The sub-beam 8 corresponds to the zero diffraction order in reflection. The diameter of the incident beam 6 is adapted to the propagation distance L of the coupled sub-beam 7 in the waveguiding layer 2. Typically, the beam width W of the incident beam 6 and the propagation distance L of the guided mode are of similar order of magnitude. The sensitivity of the sensor depends on the optical parameters of the waveguide, i.e. on the thickness and refractive index of the thin waveguiding layer as well as on the refractive indexes of substrate and superstrate. For the detection of chemical changes taking place at or in the immediate vicinity of the waveguiding layer it is advantageous to choose the thickness of the waveguiding layer 2 of high refractive index smaller than the wavelength of the coupled light.

Figure 5:
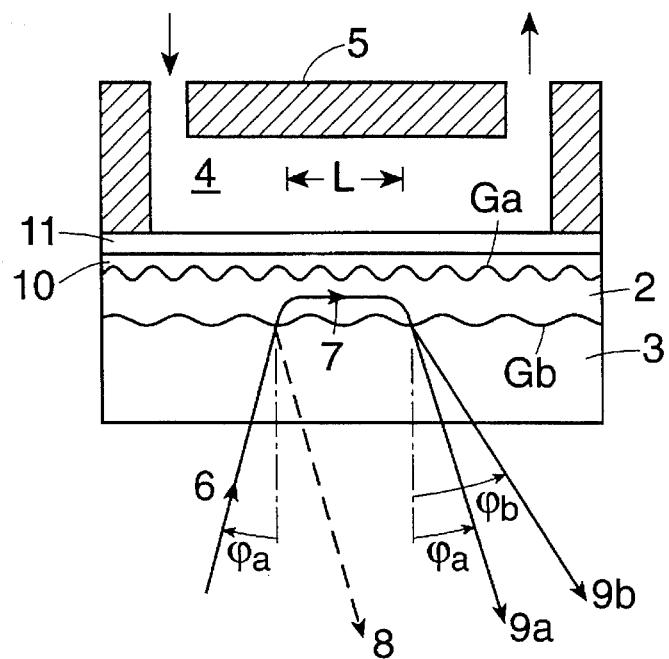
FIG. 5 is a diagrammatic section of another form of a sensor.

The planar waveguide shown in an extended diagrammatic longitudinal section in FIG. 5, modulated with two gratings Ga and Gb, is provided with a thin chemo-sensitive additional layer 10 on top of the waveguiding layer 2. The sample 4 for analysis is brought into contact with the chemo-sensitive layer 10 in the sample cell 5. The chemo-sensitive layer can be chosen from materials which bind the chemical substance being detected. For example, an antigen or antibody or other pairs of biomolecules which show complementary behavior. Other materials which selectively chemisorb or chemically bind a specific substance can be used. The resonance angles $\phi a$ and $\phi b$, at which the coupling and decoupling of the beams take place, depend upon the period lengths of the two gratings and on the effective refractive index of the mode 7 guided in the waveguide. The addition of a molecular adsorbate layer 11 to the chemo-sensitive layer 10 results in a change of the effective refractive index and/or an attenuation of the guided mode.

Figure 6:
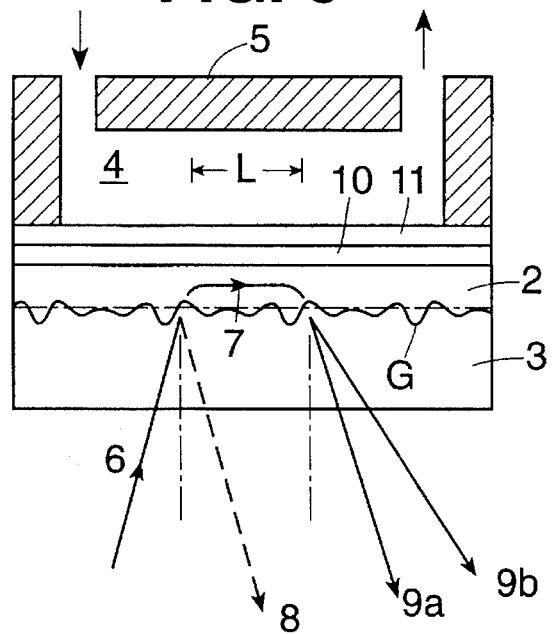
FIG. 6 is a section of a sensor comprising a grating coupler similar to that in FIG. 1b.

In the biperiodically modulated planar waveguide on a planar substrate with a sample cell as shown in a diagrammatic longitudinal section in FIG. 6, the waveguiding layer 2 is also provided with a chemo-sensitive additional layer 10 in contact with the sample 4. The resonance angles for the coupling and decoupling of the beams of light depend on the period lengths of the two Fourier components of the biperiodic grating G, and on the effective refractive index of the mode 7 propagating in the waveguide. Light adsorption by a molecular layer 11 on the surface of the chemo-sensitive layer 10 results, for example, in an attenuation of the guided mode, which can be detected by measuring the intensity of the decoupled beam 9b.

Figure 7:
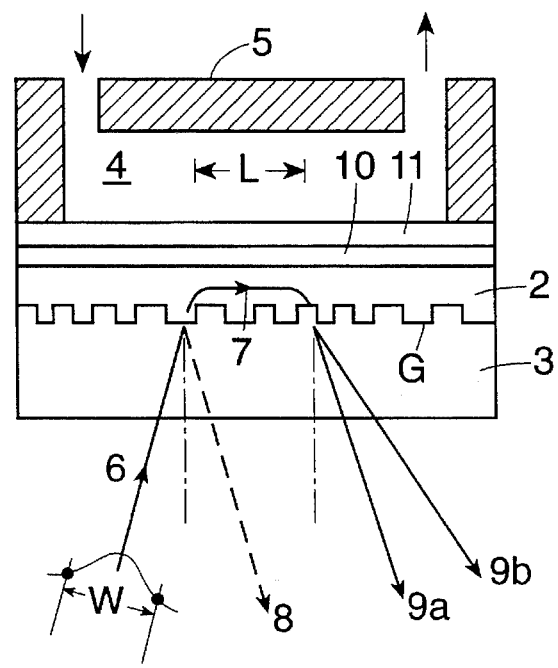
FIG. 7 is a section through sensor comprising a grating coupler similar to that of FIG. 1c.

In the biperiodically modulated planar waveguide on a substrate with a sample cell as shown in diagrammatic longitudinal section in FIG. 7, the resonance angles for coupling and decoupling of the light beams depend on the period lengths of the two gratings in the alternate grating sections Ga and Gb, and on the effective refractive index of the mode 7 guided in the waveguide. The width of the alternate grating sections Ga and Gb of different periodicity (see FIG. 1d) is preferably smaller than the diameter W of the incident beam 6. The addition of a molecular adsorbate layer 11 to the chemo-sensitive layer 10 results in a change of the effective refractive index and/or an attenuation by absorption of the guided mode 7.

The bidiffractive property of this grating structure results from the fact that the mode 7 coupled into waveguide 2 interacts with grating $G_a$ as well as with grating $G_b$, whereby decoupled sub-beams 9a and 9b are generated.

It is advantageous for the reproducibility of the measurement that the efficiency for coupling and decoupling of light is insensitive to a translation of the waveguide in the plane of the waveguiding layer with respect to the incident beam 6. This effect is obtainable to a degree which is very close to full insensitivity to such a translation by choosing the width of the alternate arranged, strip shaped grating sections $G_a$ and $G_b$ smaller than the diameter W (lateral dimension) of the incident, partially coupled light beam 6.

Since coupling of a light beam into a waveguide is a process wherein the coherence of the light plays an important role, it is advantageous that also the grating structure has a high degree of coherence. As suggested by the graphic representation in FIG. 1d and 7 a grating structure having this property is obtained by ensuring that the distance between grating elements of different grating sections $G_a$ (respectively $G_b$) constitutes a multiple of the period length of the grating type $G_a$ (respectively $G_b$).

Figure 8:
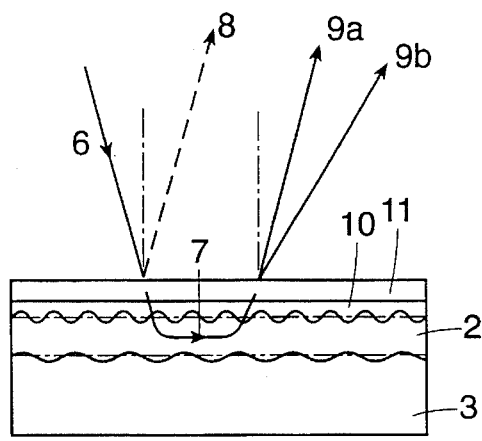
FIG. 8 is a section through a sensor and shows light coupling on the superstrate side.

The planar waveguide 1 shown in diagrammatic longitudinal section in FIG. 8 is modulated with two gratings and coated with a thin chemosensitive additional layer 10. The resonance angles for coupling and decoupling of the beam 6, which is incident on the superstrate side, depend on the period lengths of the two gratings and on the effective refractive index of the guided mode 7. The presence of an adsorbate layer 11 can be quantitatively determined, for example, by measuring the intensity of the decoupled sub-beam 9b.

Figure 9:
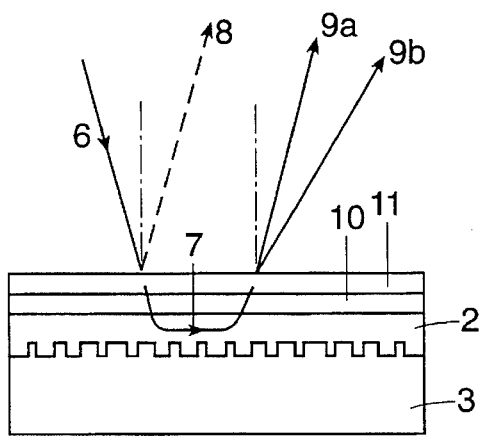
FIG. 9 is a section through a sensor comprising a grating coupler similar to that shown in FIG. 1c.

In the planar waveguide shown in longitudinal section in FIG. 9 the coupling and decoupling of the beams of light takes place on the superstrate side. The incident beam 6 is coupled via one of the evanescent waves generated by the grating structure. The coupled sub-beam propagates as a guided mode 7 in the waveguiding layer 2, thereby it is continuously decoupled again by the bidiffractive grating structure, resulting in the sub-beams 9a and 9b. The two beams 9b and 8 have different directions of propagation, beam 8 corresponds to the zero diffraction order in reflection. This directional separation enables a background-free detection of light decoupled from the waveguide mode 7. This is obtained by measuring the intensity of beam 9b. From this measurement, for example, the presence of an absorbent additional layer 11 is deduced.

Figure 10:
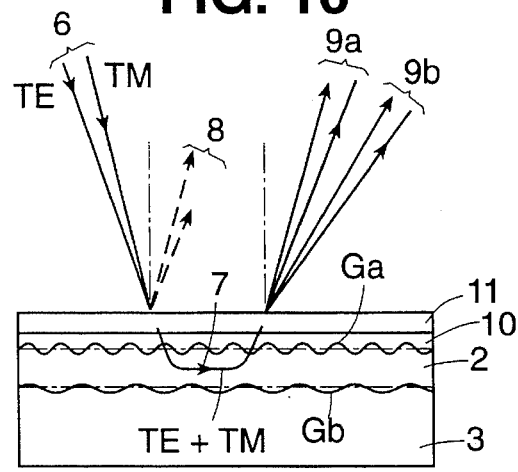
FIG. 10 is a section through a sensor and shows two light beams coupled simultaneously on the superstrate side.

The planar waveguide shown in diagrammatic longitudinal section in FIG. 10 is modulated with two gratings and coated with a chemo-sensitive additional layer 10. By simultaneously coupling of two coherent orthogonally polarized beams of light, two jointly excited modes of different polarization (TE and TM) are generated in the waveguide. The decoupled sub-beams are coherent to one another and can be brought to interference by passing through a polarizer. Measurement of the relative phase (phase difference) of two sub-beams decoupled from the two orthogonally polarized modes 7 (TE and TM) enables one to detect the presence of an adsorbate layer 11 with very high sensitivity.

An alternative detection method comprises the measurement of the relative intensity of two decoupled sub-beams. In this case the coupling of the two modes 7 in FIG. 10 and the measurement of the relative intensity of the sub-beams 9b can take place in sequence.

The chemo-sensitive layer 10 in FIGS. 5–10 is e.g. a chemo-selective layer.

If a beam of light, for example a laser beam, impinges on a waveguiding layer modulated with a grating structure, then in addition to the reflected and transmitted sub-beams other discrete diffraction orders are generated, both in reflection and in transmission. Provided that the angle of incidence is correctly chosen, the beam is coupled into the waveguide via one diffraction order. The coupled sub-beam propagates as a guided mode in the waveguiding layer and gets into interaction with the diffraction grating a second time; whereby the guided mode is continuously decoupled again.

The propagation distance required for complete decoupling of the guided mode depends on the diffraction efficiency of the grating. The grating regions in which coupling and decoupling take place are offset from one another and partially overlap. As shown diagrammatically in FIG. 4, the decoupled sub-beams 9a and 9b are laterally displaced from the incident beam 6. The ratio of the lateral displacement L to the beam width W is dependent on the profile of the beam incident on the waveguiding layer and on the diffraction efficiency of the grating [cf. T. Tamir and H. L. Bertoni, "Lateral displacement of optical beams at multilayered and periodic structures", J. Opt. Soc. Am. 61 (1971), pp. 1397–1413; and T. Tamir and S. T. Peng, "Analysis and Design of Grating Couplers", Appl. Phys. 14, pp. 235–254 (1977)].

If the mode guided in the waveguide is coupled and decoupled via one and the same grating, the decoupled beams propagate parallel to one of the direct diffraction orders of the beam incident on the grating. By the use of two (or more) superposed gratings having different periodicities and/or orientations, however, it is possible to couple and decouple a beam of light into and from a waveguide, whereby the direction of at least one decoupled sub-beam differs from the directions of the reflected, transmitted and directly diffracted sub-beams, which are generated by the incident beam of light.

FIGS. 4 to 10 show this diagrammatically for different types of biperiodic grating structures: the incident beam of light 6 is coupled into the waveguide via the first diffraction order of the grating Ga; the coupled beam 7 propagates in the waveguiding layer, whereby it is continuously decoupled by the two superposed gratings Ga and Gb, so that two sub-beams 9a and 9b are generated with different directions of propagation. The directional separation of the decoupled sub-beam 9b from the sub-beam 8, which is generated by reflection of the incident beam 6, enables a background-free detection of decoupled light although the grating regions in which coupling and decoupling take place overlap in part.

The following paragraphs describe characteristic methods, apparatusses, embodiments, and advantages of this invention:

1. A planar optical waveguide comprising a waveguiding layer on a planar substrate, which is modulated with a multi-diffractive, e.g. biperiodic, grating structure, is brought into contact with a sample for analysis. The multi-diffractive grating structure consists, for example, of two gratings of different periodicity and/or orientation arranged one above the other or alternately or superposed, enabling accurate analysis to be made.

2. By means of the above described multi-diffractive grating structure, beams of light are coupled into and decoupled from the waveguide; in these conditions decoupled sub-beams are generated whose propagation directions do not coincide with the direct diffraction orders of the beams incident on the grating structure. In particular, the directions of these decoupled subbeams are different from the zero diffraction order, i.e. from the directions of the fractions of the incident light beam reflected at (or transmitted through) the waveguiding layer.

3. Although the regions on the waveguiding layer in which coupling and decoupling of the beams take place partially overlap, the beams reflected at (or transmitted through) the waveguiding layer are separated from at least one sub-beam decoupled from the waveguide.

4. The multi-diffractive grating modulation of the waveguiding layer is homogeneous in the plane of the layer; i.e. the efficiency for coupling and decoupling the light is insensitive to translation of the waveguide in the plane of the waveguiding layer with respect to the incident beam of light.

5. Coupled beams of light propagate as guided modes in the waveguiding layer and interact with a chemo-sensitive surface layer and/or a sample covering the planar waveguide on the superstrate side.

6. Chemical changes (e.g. molecular additions) at or in the immediate vicinity of the waveguiding layer are detected by measuring the (relative) intensity of one or more decoupled sub-beams.

7. Two coherent (e.g. orthogonally polarized) beams of light are simultaneously coupled into and decoupled from the waveguide by means of the multidiffractive grating structure and two decoupled sub-beams are brought to interference, e.g. by means of a polariser. The proof of chemical changes, e.g. molecular additions, at or in the immediate vicinity of the waveguiding layer is effected by measuring the relative phase (phase difference) of two decoupled sub-beams generated by the two simultaneously guided (orthogonally polarized) modes.

8. Chemical or physical effects on the waveguiding layer taking place outside the coupling and decoupling regions have no influence on the light guided in the waveguide and used for the measurement.

9. By integration of different measuring locations on the surface of a multi-diffractively modulated planar waveguide e.g. in a two-dimensional raster, a number of substances in a sample are detected in parallel or in sequence on one and the same planar test substrate.

I claim:

1. A microoptical sensor for detecting chemical substances, the sensor comprising:

a) a solid substrate;

b) a planar waveguide layer located on a surface of the substrate, the planar waveguide layer having an interaction surface for contacting the chemical substances to be detected; and c) a diffractive grating located proximate to the planar waveguide layer for coupling and decoupling light into and out of the planar waveguide layer, the diffractive grating comprising at least two superimposed gratings, (i) a first grating having a first fixed fundamental frequency and a first discrete diffraction order, the first grating acting as an input grating coupler for coupling light into the planar waveguide layer at a first discrete coupling angle, the incoupled light interacting with the chemical substances adjacent to the interaction surface and (ii) a second grating having a second fixed fundamental frequency different from the first fundamental frequency and a second discrete diffraction order different from the first diffraction order, the second grating acting as an output grating coupler for coupling light out of the planar waveguide layer at a second discrete coupling angle different from the first coupling angle, the first and second discrete coupling angles causing a detectable directional separation of light coupled into and out of the planar waveguide layer, thereby enabling background-free detection of the light coupled out of the waveguide layer.

2. The microoptical sensor of claim 1, wherein said planar waveguide layer is provided with a chemo-selective or chemo-sensitive coating on the interaction surface.

3. The microoptical sensor of claim 2, wherein the thickness of the planar waveguide layer is smaller than the wavelength of the coupled light.

4. The microoptical sensor of claim 1 wherein said diffractive grating comprises a plurity of spaced parellel relief gratings having different periodicities or orientations 5. The microoptical sensor of claim 1, wherein said diffractive grating comprises a number of superposed relief gratings having different periodicities or orientations.

6. The microoptical sensor of claim 1, wherein the diffractive grating comprises grating elements, and wherein the width of the grating elements varies periodically.

7. The microoptical sensor of claim 1, wherein the diffractive grating comprises grating elements, and wherein the depth of the grating elements varies periodically.

8. The microoptical sensor of claim 1, wherein said grating diffractive grating comprises a relief grating produced by means of a multi-stage lithographic process in which a number of surface relief gratings having different periodicities and/or orientations are etched in sequence into said substrate surface.

9. The microoptical sensor of claim 1, wherein said diffractive grating is produced holographically.

10. The microoptical sensor of claim 1, wherein said diffractive grating comprises parallel, strip-shaped, alternate arranged sections of two gratings ($G_a$, $G_b$) which have different periodicities or orientations.

11. The microoptical sensor of claim 10, wherein the width of the parallel, strip-shaped, alternate arranged grating sections ($G_a$, $G_b$) is smaller than the diameter (lateral dimension) of the incident, light beam.

12. The microoptical sensor of claim 10, wherein the width of the parallel, strip-shaped, alternate arranged grating sections ($G_a$, $G_b$) is smaller than the propagation distance of the guided mode within which the coupling and decoupling of light occurs.

13. A microoptical sensor according to claim 10, wherein the individual strip-shaped grating sections had the same periodicity and orientation and are so arranged with respect to each other, that the distances between grating elements of different grating sections having the same periodicity and orientation is a multiple of the period length of this grating type.

14. The microoptical sensor according to claim 1, wherein the diffractive grating is transferred by an embossing process from a multi-diffractive master grating to the surface of a substrate to which the high-refraction waveguiding layer of high refractive index is applied.

15. The microoptical sensor according to claim 14, wherein the multi-diffractive master grating is produced by means of a multi-stage lithographic process or holographically.

16. A microoptical method for detecting chemical substances with a microoptical sensor as defined in claim 1, which method comprises a) contacting the interaction surface of the planar optical waveguide layer with a sample containing the substance to be detected, b) coupling coherent light into said waveguiding layer, which light propagates therein as a guided light wave, c) then decoupling said light wave out of the waveguiding layer, and analyzing the decoupled light.

17. The microoptical method of claim 16, wherein a number of beams of light whose relative intensity is measured are coupled into and decoupled from the planar waveguide layer.

18. The microoptical method of claim 17, wherein the measured beams of light have different polarizations.

19. The microoptical method of claim 17, wherein the measured beams of light have different wavelengths.

20. The microoptical method of claim 16, wherein a plurality of coherent beams of light whose relative phase is measured are coupled into and decoupled from the planar waveguide layer.

21. The microoptical method of claim 20, wherein the measured beams of light have different polarizations.

* * * * *

UNITED STATES PATENT AND TRADEMARK OFFICE
CERTIFICATE OF CORRECTION

PATENT NO. : 5,455,178
DATED : October 3, 1995
INVENTOR(S) : Christof Fattinger

It is certified that error appears in the above-indentified patent and that said Letters Patent is hereby corrected as shown below:

In Column 11, claim 8, line 2, delete first word, "grating".

In column 12, claim 16, line 4, delete last word, "optical".

Signed and Sealed this

Ninth Day of January, 1996

Attest:

BRUCE LEHMAN

Attesting Officer

Commissioner of Patents and Trademarks